US008843505B2

(12) United States Patent
Campbell et al.

(10) Patent No.: US 8,843,505 B2
(45) Date of Patent: Sep. 23, 2014

(54) HEALTHCARE RECORD SYSTEM AND METHOD FOR PROVIDING IMPROVED PORTABLE DATA

(75) Inventors: Janet L. Campbell, Madison, WI (US); Dustin L. Gage, Madison, WI (US); Brian M. Weisberger, Madison, WI (US)

(73) Assignee: Epic Systems Corporation, Verona, WI (US)

( * ) Notice: Subject to any disclaimer, the term of this patent is extended or adjusted under 35 U.S.C. 154(b) by 333 days.

(21) Appl. No.: 12/753,241

(22) Filed: Apr. 2, 2010

(65) Prior Publication Data

US 2010/0257189 A1 Oct. 7, 2010

Related U.S. Application Data

(60) Provisional application No. 61/166,596, filed on Apr. 3, 2009.

(51) Int. Cl.
| | | |
|---|---|---|
| G06F 17/30 | (2006.01) | |
| G06F 7/00 | (2006.01) | |
| G06Q 50/22 | (2012.01) | |
| G06Q 10/10 | (2012.01) | |
| G06Q 50/24 | (2012.01) | |
| G06F 19/00 | (2011.01) | |

(52) U.S. Cl.
CPC .............. *G06Q 50/22* (2013.01); *G06F 19/323* (2013.01); *G06F 19/322* (2013.01); *G06Q 10/10* (2013.01); *G06Q 50/24* (2013.01)
USPC .......................................... 707/758; 715/743

(58) Field of Classification Search
USPC ........................................... 707/758; 715/743
See application file for complete search history.

(56) References Cited

U.S. PATENT DOCUMENTS

| | | | | |
|---|---|---|---|---|
| 6,873,960 | B1 * | 3/2005 | Wood et al. ....................... | 705/4 |
| 7,043,754 | B2 * | 5/2006 | Arnouse .......................... | 726/20 |
| 7,520,419 | B2 * | 4/2009 | Libin et al. .................... | 235/375 |
| 7,730,159 | B1 * | 6/2010 | Meyer et al. .................. | 709/217 |
| 7,925,519 | B2 * | 4/2011 | Greene ............................ | 705/2 |
| 7,949,546 | B1 * | 5/2011 | Klieman et al. ................ | 705/3 |
| 8,010,385 | B1 * | 8/2011 | Henderson ....................... | 705/3 |
| 8,150,714 | B2 * | 4/2012 | Prescott ........................... | 705/4 |
| 2002/0080189 | A1 * | 6/2002 | Dvorak et al. ................ | 345/810 |
| 2005/0010796 | A1 * | 1/2005 | Arnouse ........................ | 713/200 |
| 2005/0055560 | A1 * | 3/2005 | Kendon ......................... | 713/189 |
| 2005/0108634 | A1 * | 5/2005 | Sahota et al. ................. | 715/513 |
| 2006/0053411 | A1 * | 3/2006 | Takamiya ..................... | 717/115 |
| 2007/0138253 | A1 * | 6/2007 | Libin et al. .................... | 235/375 |
| 2008/0033751 | A1 * | 2/2008 | Greene ............................ | 705/2 |
| 2008/0120145 | A1 * | 5/2008 | Prescott .......................... | 705/4 |

* cited by examiner

Primary Examiner — Pavan Mamillapalli
(74) Attorney, Agent, or Firm — Boyle Fredrickson, S.C.

(57) ABSTRACT

A health-data-portal aggregator executing a stored program to accept medical information entered by the patient for storage on the electronic computer, upload electronic clinical records generated by a healthcare institution in electronic format viewable in a browser interpreting HTML, and generate a downloaded index file in a format viewable in a browser interpreting HTML, the index file including patient medical data selected from at least one of: (1) the medical information from the patient and (2) the clinical records of the patient and accessible by at least one HTML link.

21 Claims, 6 Drawing Sheets

PERTINENT MEDICAL INFORMATION

PATIENT: EDITH SONGBIRD
MyChartCentral.COM | READ ME
CURRENT AS OF SATURDAY, MAY 02, 2009

ALLERGIES    MILK
MEDICATIONS  CELEXA
NOTES        PLEASE CALL MY HUSBAND IF I'M EVER IN AN ACCIDENT. HIS CELL NUMBER IS
             608 770 4949, WORK IS 608 251 0251, HOME IS 608 268 5719.

MEDICAL DOCUMENT LIBRARY
                                          PREPARED ON SATURDAY, MAY 02, 2009

YOUR MEDICAL DOCUMENT LIBRARY MAY CONTAIN BOTH HEALTH SUMMARIES THAT HAVE BEEN
CREATED BY CLINICIANS AND ORGANIZATIONS THAT PROVIDE YOU WITH MEDICAL CARE AND
PERSONAL HEALTH INFORMATION YOU ENTERED YOURSELF. CLICK ON A LINK BELOW TO VIEW
ONE OF YOUR DOCUMENTS.

THE DOCUMENTS LISTED WERE PASSWORD PROTECTED WHEN DOWNLOADED.
IF THE LINKS BELOW DON'T WORK, UNZIP MY_DATA.ZIP, FOUND HERE.
TO LEARN MORE ABOUT HOW TO UNZIP, CLICK HERE.
BE SURE TO DELETE THE UNZIPPED FOLDER WHEN YOU ARE FINISHED SO THEY CAN STAY PROTECTED.

IHE_XDM>MY_DATA

LUCY PATIENT SUMMARY FROM 5/2/2009          [CHECK IF CURRENT]
    METRO MEDICAL MY CHART FROM 2/25/2009       [CHECK IF CURRENT]
    NEW WORLD HEALTH CARE RECORD XPHR SUMMARY FROM 2/10/2009  [CHECK IF CURRENT]

COPYRIGHT©2009 EPIC SYSTEMS CORPORATION | FAQ | REQUEST HELP | PRIVACY POLICY | TERMS OF SERVICE

180
HEALTHCARE RECORD SYSTEM AND METHOD FOR PROVIDING IMPROVED PORTABLE DATA

CROSS REFERENCE TO RELATED APPLICATIONS

This application claims the benefit of U.S. provisional application 61/166,596 entitled: Healthcare Record System Providing Improved Portable Data" filed Apr. 3, 2009, hereby incorporated by reference.

BACKGROUND OF THE INVENTION

The present invention relates to electronic medical records and, in particular, to a system and method for improving the accessibility of electronic medical records stored on removable media.

Personal health record (PHR) websites allow a patient to record patient-sourced health data and provide general health-related information. A patient may use a PHR site, for example, to keep a healthcare diary, record medications, track information such as weight or blood pressure, etc. These personal health record sites serve a valuable purpose in preserving patient-sourced data.

These sites may also provide continuity in a patient's medical information recordkeeping when healthcare providers are changed or multiple healthcare providers are used. Some personal health record sites allow data to be uploaded from electronic portals of healthcare institutions, or are an integral part of the medical record system of the healthcare institution. This inclusion of the medical record system data means that the PHR site may serve as a centralized health record repository for the patient while the patient is a patient of the healthcare institution. One example of such a system is the MyChart PHR system provided by the Epic Systems Corporation of Verona, Wis. and described in United States Patent Application 20030208381 filed Mar. 29, 2001 and entitled: Patient Health Record Access System, incorporated herein by reference.

Such personal health record sites may provide a variety of features to help the patient organize and understand his medical data. The specific features may vary widely between implementers of the personal health record sites. Exemplary features include data organization, data augmentation, inclusion of image files, data mining capabilities, etc.

The uploading of a patient's medical data to a PHR is greatly facilitated by emerging standards for electronic medical records which define standard formats for such data. Standardized formats allow the data to be readily integrated into the familiar environment of the PHR. Generally, such standards are designed to promote continuity in a patient's healthcare records as the patient moves between healthcare providers over the course of his or her life. Ideally, a universal standard or set of translatable standards allows patients to easily transfer their electronic medical files to a new healthcare provider, for example over the Internet, as the patients change healthcare providers.

Current standards for electronic medical records anticipate that some data transfers will employ removable storage media such as optical disks or flash memory drives (thumb drives) receiving downloaded electronic medical records that are then physically transported by the patient. The downloaded files, formatted for storage on such media, may include a human readable index file to assist the end user in identifying the files and uploading them to an electronic medical record system at a receiving institution. This index file can be formatted, for example in HTML, for viewing on a standard browser.

BRIEF SUMMARY OF THE INVENTION

The present inventors have recognized that the index file, normally associated with health record files stored in removable media, can be simply augmented to provide many of the familiar features of the patient's PHR when the files are read using a standard browser. With these modifications, the accessibility of such downloaded files to an ordinary patient can be greatly increased, permitting the patient or the patient's healthcare provider to use the files much like a standard PHR when Internet accessibility is impractical, intermittently available, or unavailable. By incorporating HTML or XML stylesheets suitable for the downloaded file types, text, images, and improved file descriptions, the downloaded files may approximate the look and feel of the PHR, giving the patient a familiar environment and interpretive clues to help him use these files effectively when the more complete environment of the PHR is unavailable. By preserving links to the patient's PHR when Internet access is available, the value of the downloaded data to the patient may be enhanced with an on-line service confirming that the data is up-to-date, updating data, or the like. The downloaded data may carry with it information used to populate portions of an authentication mechanism of the PHR site allowing rapid access to the PHR site when needed. In this way, offline data can become another important access point by patients to their medical records, increasing the involvement of patients with their health care and thereby promoting better health care outcomes.

DETAILED DESCRIPTION OF THE PREFERRED EMBODIMENT

Figure 1:
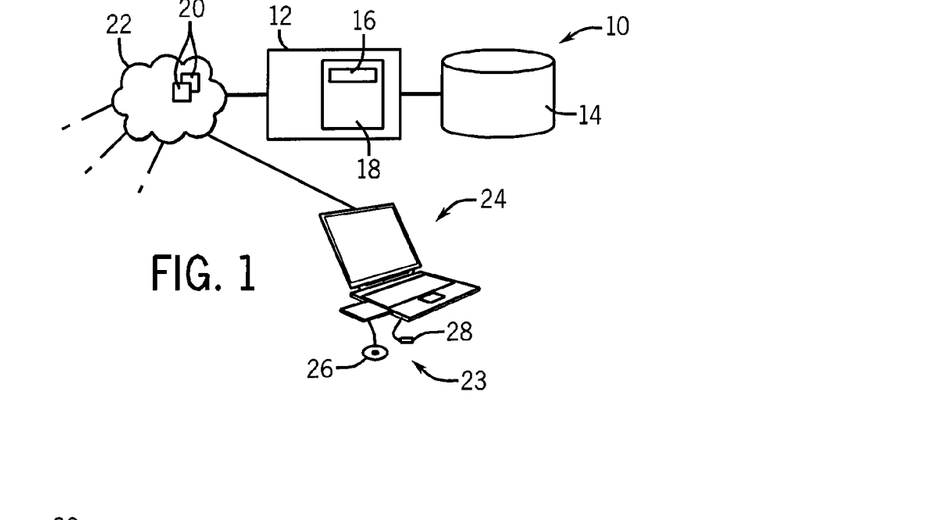
FIG. 1 is a diagram showing the interconnection of a personal health record (PHR) server computer and patient client computers to implement a PHR website.

Referring now to FIG. 1, a personal health record (PHR) website 10 may include an electronic computer 12 of the type well known in the art communicating with a mass storage device 14 such as a disk drive array to implement a database linked to a Web server according to a stored PHR program 16 stored in an electronic memory 18 of computer 12.

PHR website 10 may be configured to serve a set of web pages 20 on the Internet 22 providing a display of information to patients, including, for example, medical data entered by the patient and stored on the mass storage device 14, uploaded clinical medical data, and links to informative medical articles. The web pages 20 may also provide tools for monitoring and displaying patient health programs and activities, as well as providing portal connections to healthcare institutions permitting, for example, the patient to make appointments, track lab test results, query physicians, and receive notifications for activities and/or informational articles relevant to the patient sponsored by the healthcare institution.

Connection with the PHR website 10 is provided by a standard browser program (not shown), for example, executing on a personal computer 24 under control of the patient that is connected with the Internet 22 to receive the web pages 20. The personal computer 24 may accept removable media 23, such as CD-ROM 26 or USB memory sticks 28 or the like, for reading from and writing to such removable media 23.

Computer 24 may be configured to use the removable media 23 to store portable medical records from a PHR database of a previous medical record system, stored on mass storage device 14 and including clinical medical records and patient-sourced medical data. The portable medical records may be stored in any of a variety of different forms including a Continuity of Care Document (CCD), being an XML-based markup standard specifying a standard for the encoding, structure and semantics of medical information. The standard requires that the stored records include a human-readable textual portion, which allows interpretation of the records without the benefit of their inclusion in a medical record system) and one or more structured portions for software processing by medical record systems that will allow the records to be easily uploaded to a new medical record system. The human-readable textual portion contains a textual version of a patient's medical record including administrative, demographic, and clinical information facts about a patient's healthcare covering one or more healthcare encounters from a medical provider, the patient-sourced medical data, etc.

The Continuity of Care Document provides a means for one healthcare practitioner, system, or setting to aggregate all of the pertinent data about a patient and forward it to another practitioner, system, or setting to support the continuity of care. Its primary use case is to provide a snapshot in time containing the pertinent clinical, demographic, and administrative data for a specific patient. In a continuity of care document, the human-readable textual portion is combined with the structured portion in a single XML-based document.

As is generally understood in the art, XML provides for text tags that demarcate types of content within a text data file. The resulting XML file is generally human readable but designed to be machine interpretable and thus is difficult for many patients to understand. The computer 24 may upload medical data from the removable media 23 to the PHR website 10 and conversely may also be used to receive downloaded data from that PHR website 10.

Figure 2A:
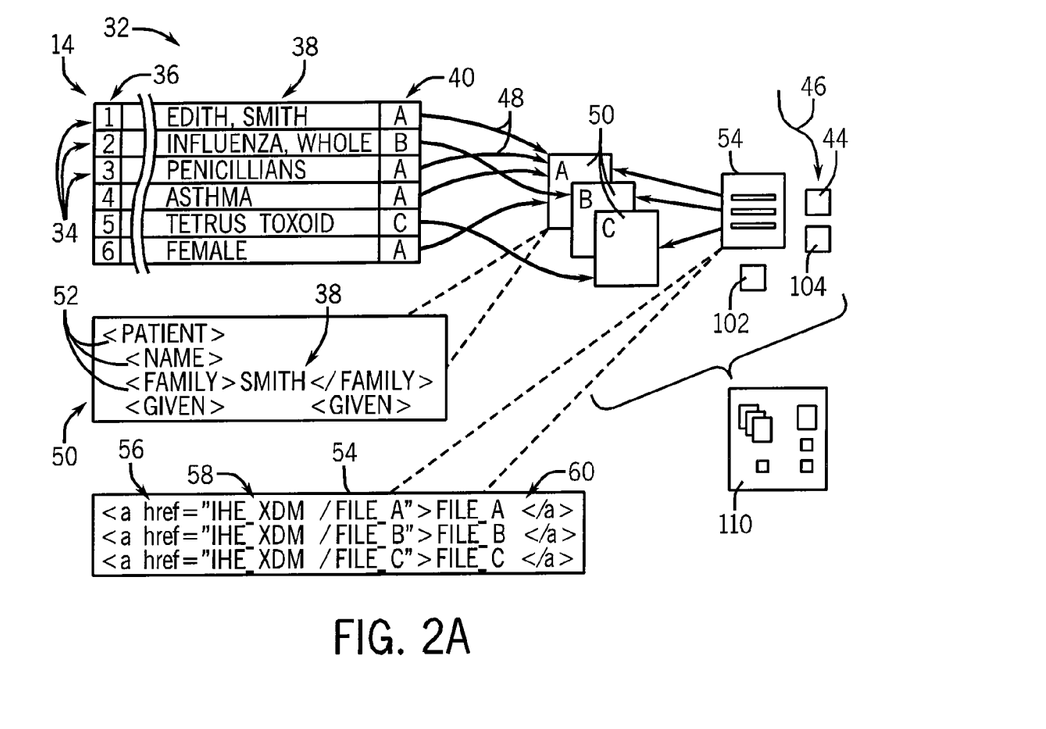
FIG. 2A is a data flow diagram showing extraction of data from medical records held by the PHR into downloadable medical data files and an index file.
Figure 2B:
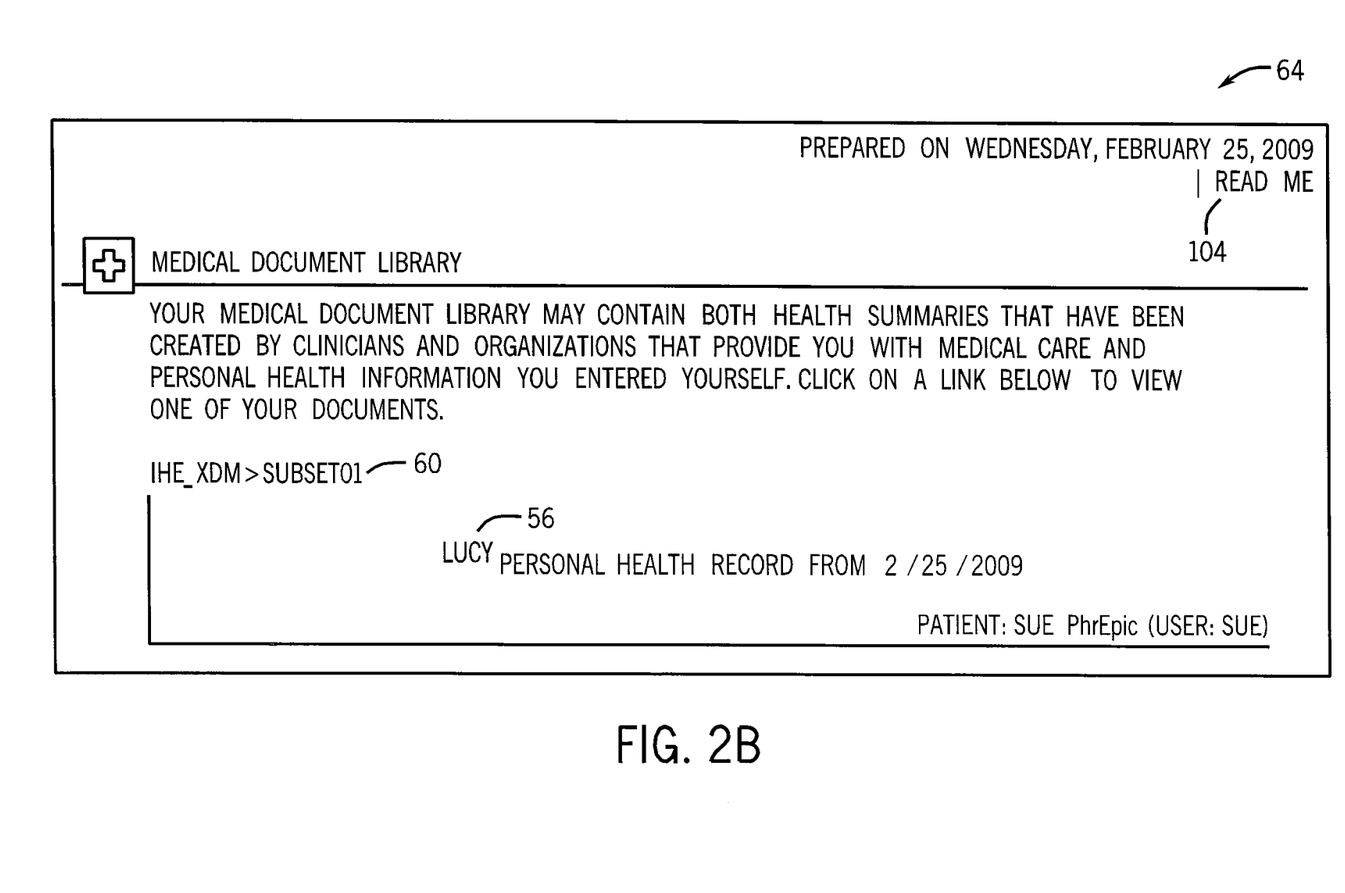
FIG. 2B is an exemplary index file created in the data flow of FIG. 2A.
Figure 4:
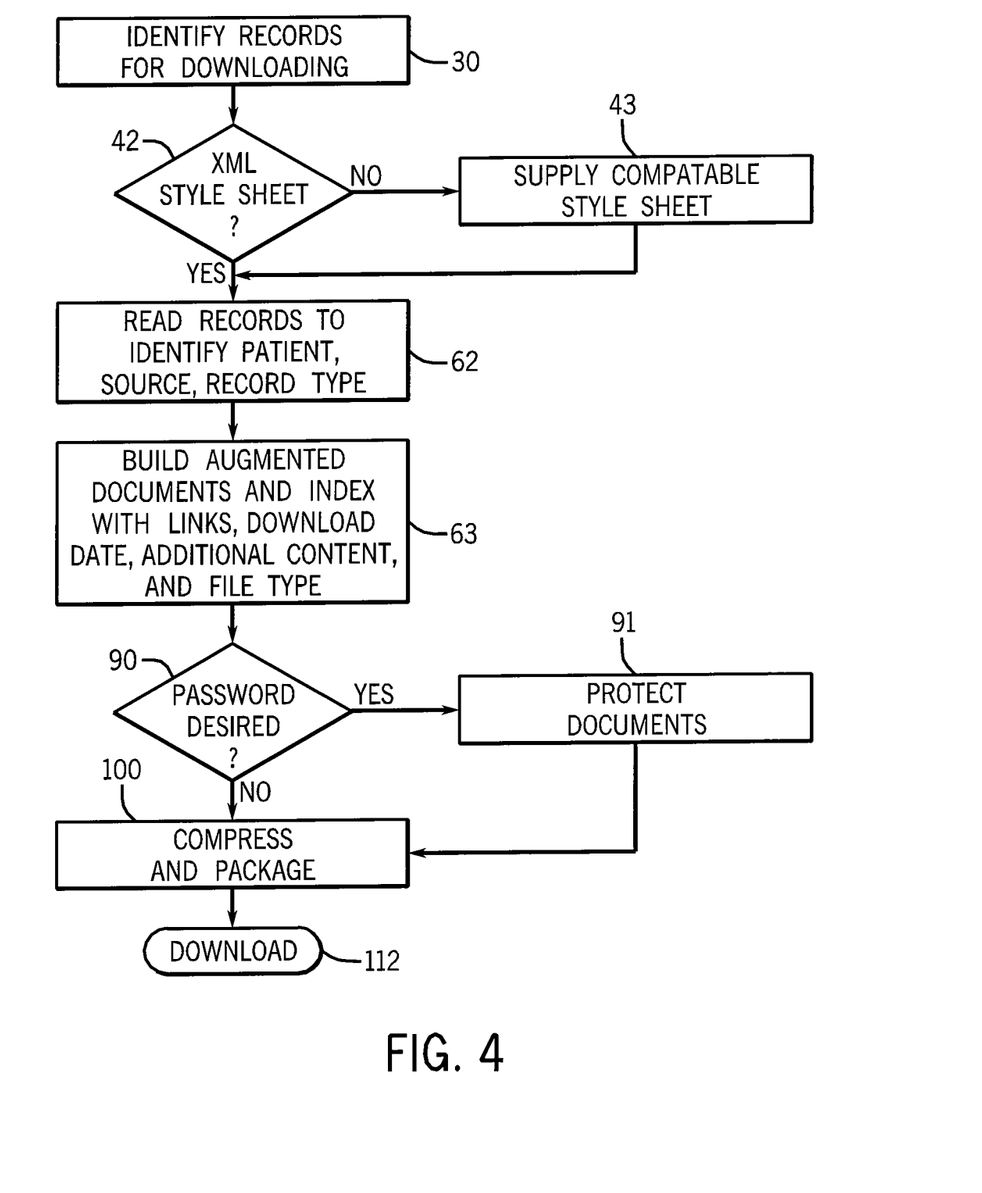
FIG. 4 is a flow chart of the steps executed by the PHR server computer of FIG. 1 to implement the augmentation of FIG. 3.

Referring now to FIGS. 2 and 4, in this latter situation, commands from the browser executing on the computer 24 (and sent to computer 12) may be used to initiate a downloading of medical data from the PHR database, shown as database 32 in FIG. 2A, per process block 30. This downloading process is normally preceded by authentication steps in which the patient provides a user name and password and logs onto the PHR website 10 to obtain access to medical data associated with the patient or persons related to or under the care of the patient. The computer 12 executing the PHR program 16 may then provide a list of downloadable medical data files to the patient allowing him or her to select particular files for downloading.

These files available for downloading may be files that were previously uploaded in a standard format (such as CCD) or that are newly created based on healthcare encounters from a healthcare institution and held as such or incorporated into the database, may be data sourced by the patient him or herself and incorporated into the database 32, may be data uploaded from healthcare provided by other healthcare institutions, etc.

Generally the database 32 will comprise a set of records 34 each having a unique record identifier 36, a field indicating a type of medical data of the record (not shown), the value of the medical data 38 of the records, and the data source 40 of the medical data 38 (e.g., a hospital or clinic name or the patient). In this example, the data source may be the patient (A) or different medical institutions (B) and (C).

Types of medical data may include allergies, current medications, medical conditions, immunization history, care history, care providers, health concerns and the like.

For example, in selecting the particular files to be downloaded, the patient may opt to download medical data 38 from each of the sources (A-C). Alternative data selection techniques are also contemplated; for example, selecting medical data by date range or medical data type or the like. The selected data 38 may be taken from the integrated database 32 or, alternatively or in addition, from previously uploaded files maintained separately, for example, as original CCD documents.

The selected records 34, as indicated by arrows 48, may then be interpreted into a standard format for downloading, for example as CCD documents. In this process, the data 38 is organized and tagged with XML tags according to the CCD standard and incorporated into one or more downloadable medical data files 50. Generally, PHR program 16 may be configured to create medical data files 50 using text string medical data 38 from the records 34 and flanking this text with the appropriate XML tags 52 derived from the type of medical data recorded in the record 34. Examples may include allergies, current medications, medical conditions, immunization history, care providers, health concerns and the like. For example, an allergy stored in the system as "Allergy 35" might be expanded in XML to:

```
<entry>
    <act classCode="ACT" moodCode="EVN">
        <templateId root="2.16.840.1.113883.10.20.1.27"/>
        <templateId root="1.3.6.1.4.1.19376.1.5.3.1.4.5.1"/>
        <templateId root="1.3.6.1.4.1.19376.1.5.3.1.4.5.3"/>
        <templateId root="2.16.840.1.113883.3.88.11.32.6"/>
        <id extension="52" root="1.2.840.114350.1.13.123.1.7.2.768076"/>
        <code nullFlavor="NA"/>
        <statusCode code="active"/>
        <effectiveTime>
            <low value="20000101"/>
```

```
        </effectiveTime>
        <entryRelationship inversionInd="false" typeCode="SUBJ">
            <observation classCode="OBS" moodCode="EVN"
negationInd="false">
                <templateId root="1.3.6.1.4.1.19376.1.5.3.1.4.5"/>
                <templateId root="1.3.6.1.4.1.19376.1.5.3.1.4.6"/>
                <templateId root="2.16.840.1.113883.10.20.1.28"/>
                <templateId root="2.16.840.1.113883.10.20.1.18"/>
                <templateId extension="allergy" root="1.3.6.1.4.1.19376.1.5.3.1"/>
                <id extension="52" root="1.2.840.114350.1.13.123.1.7.2.768076"/>
                <code code="ALG" codeSystem="2.16.840.1.113883.5.4"
                    codeSystemName="ObservationIntoleranceType"
                    displayName="Allergy">
                    <originalText>
                        <reference value="#ALG1NAM"/>
                    </originalText>
                </code>
                <statusCode code="completed"/>
                <effectiveTime>
                    <low value="20000101">
                    <high nullFlavor="PINF"/>
```

Alternatively, where the original uploaded CCD documents are preserved, those documents may be used as at least some of the medical data files 50. Generally multiple medical data files 50 may be created logically related to the request or the data organization at the PHR website 10. According to an exemplary embodiment, each file may be associated with a unique source of data.

Once the medical data files 50 have been populated with the desired information, an index file 54 is created. The index file 54 is an HTML file providing an HTML link 56 holding an index-relative address 58 for each of the medical data files 50 and a machine generated filename 60. Referring now to FIG. 2B, an exemplary index file 54 including an HTML link 56 labeled "Lucy" is shown. The index file 54 is designed to be opened in a browser and to direct a user to the particular medical data files 50 using standard browser operations (e.g., clicking on the hyperlinks 56) to permit viewing of the different medical files 50. Typically, the browser will render the data of the files 50 as unformatted text showing the XML tags and the medical data 38 as depicted in FIG. 2A.

The above-described initial stages of this process may, for example, conform to the teachings of the IHE ITI (Integrating the Healthcare Enterprise) technical framework revision 5.0, hereby incorporated by reference. This standard describes the format and file types, including the index file 54 and a ReadMe file 104, describing the source of the download for removable media 23.

The present inventors have recognized that the choice of encoding mechanisms (HTML, XML), which provide machine readability and file verification using any standard browser, creates the possibility of augmenting these files, in particular the index, to leverage the other capabilities of the browser in making this data readily accessible to the patient outside of the PHR website structure.

Referring still to FIGS. 2A and 4, the present invention first evaluates the medical data files 50 to associate one or more of the files 50 with an XML stylesheet 44 matched to the file type (e.g., CCD). Specifically, when a particular record is selected, as indicated by process block 42, the PHR program 16 checks to see whether the data when originally uploaded was associated with an XML stylesheet. Normally there will be no XML stylesheet for patient-entered data (A) and often there will be no XML stylesheet associated with data obtained from institutions (B)-(C) intending the data primarily for uploading to another institution's electronic medical record system. In these cases, an appropriate XML stylesheet 44 is generated (or selected from a library) as indicated by arrow 46 (and process block 43) to be included in files to be downloaded. Alternatively, any existing XML stylesheet may be replaced with a new stylesheet 44 providing a look and feel to the data consistent with the PHR website 10.

Figure 3:
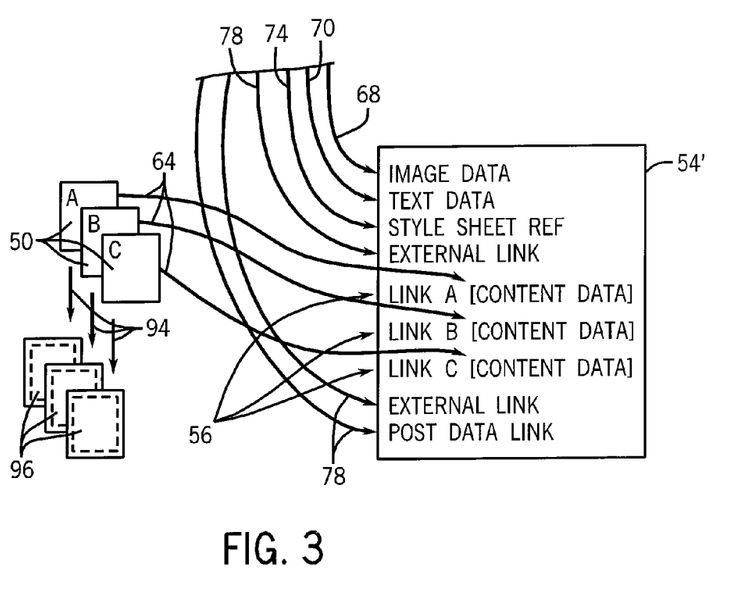
FIG. 3 is a data flow diagram similar to that of FIG. 2A showing augmentation of the index file and added downloaded files for enhanced remote user accessibility per the present invention.

Referring now to FIGS. 3 and 4, as indicated by process block 62, the PHR program 16 reviews the contents of the medical data files 50 and, as indicated by arrows 64, renames the links 56 in the index file 54' using specific content data so as to provide the user with a better understanding of the type of data associated with each of the medical data files 50. For example, the data source 40 for the medical data files 50, the type of document (e.g., a CCD document) deducible from the document header or selected by the PHR program 16, and the time range of the data of the medical data files 50 may be extracted from the medical data files 50 and used to label the links 56 as indicated by process block 63.

Figure 5:
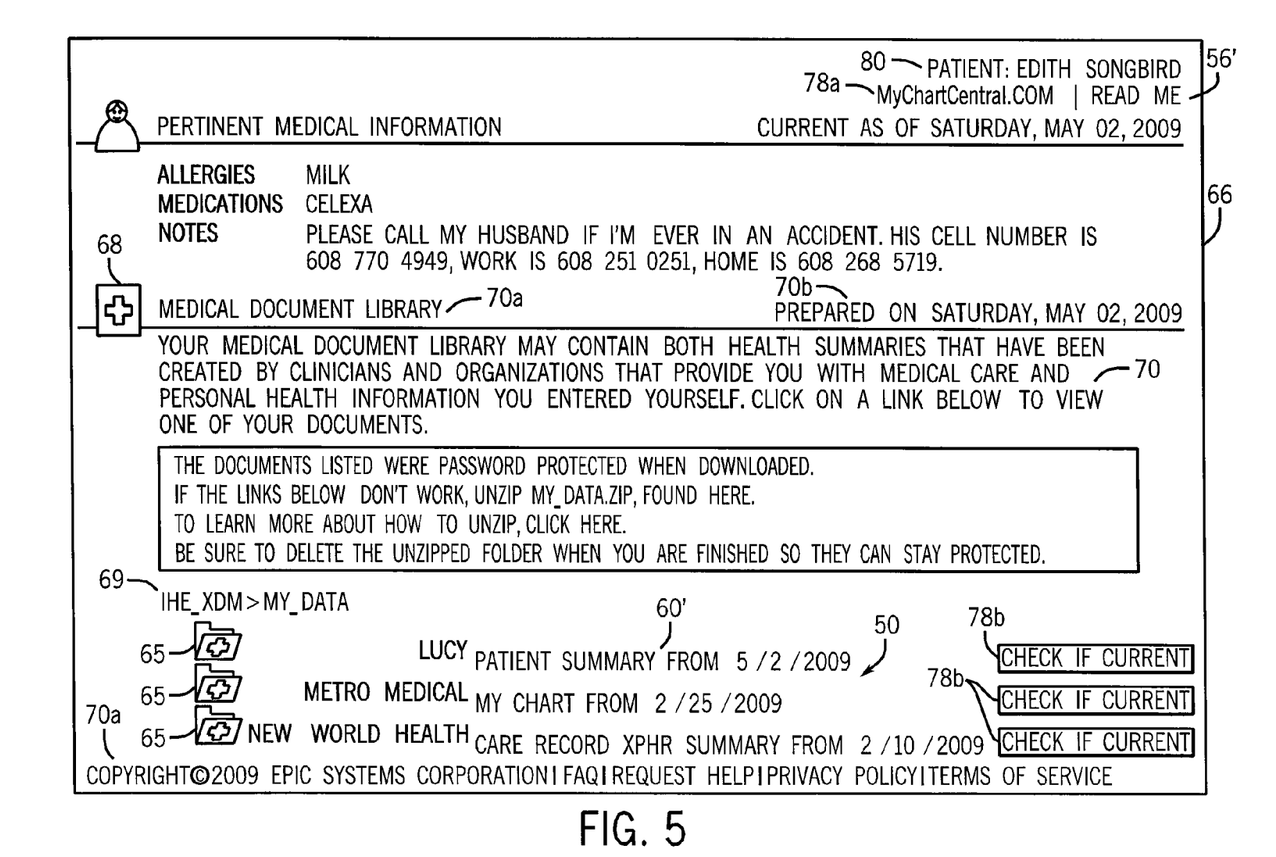
FIG. 5 is an example index file augmented per the present invention as displayed on a standard browser.

Specifically, referring to FIG. 5, an augmented index file 54' may be displayed on a browser to produce display 66 presenting augmented filename 60' now indicating the type of document (i.e., "Continuity of Care Document") and a Date Range (i.e., "2/26/2009") providing information about the medical data files 50 of greater assistance to the patient than a machine generated title. In addition, the data source 40 of the data of the medical data files 50 may be used to provide a heading 65 grouping medical data files 50 deriving data from similar sources. In this way, the index file 54 may be augmented to provide greater information about the particular medical data files 50 in an automatic fashion. The actual filename 69 of the data on the media 23 may also be provided but given a lesser prominence based on its reduced value to the patient.

Other files mandated by the standards but of lesser interest to the user may be indexed in a less prominent location and with smaller font, for example the "README" file 104 referenced by link 56'. The README file in the IHE standard provides data source information, and this data is incorporated into the index (as just described) reducing the relevance of this file to the patient while providing a more straightforward presentation of the data.

As shown in FIGS. 3 and 5, the index file 54 may be further augmented by the introduction of image data 68, ideally reflecting the same visual themes experienced by the patient when using the PHR website 10, thereby providing a consistent and familiar contextual environment for the data. Text 70 may be added explaining to the patient the purpose of the index and the scope of the indexed data of the medical data files 50. The text 70 may also include headings and standard legends 70a, as well as context information generated during the creation of the medical data files 50, for example the date of file creation and the name of the patient 70b, completing the patient experience and reinforcing the patient's understanding of the data. A stylesheet reference 74 associated and stored with the downloaded documents and referenced by the index file 54 may be used to further provide this consistent look and feel of the index file 54.

Importantly, the augmentation of the index file 54 may provide for one or more external links 78a to the patient's PHR allowing the patient to review the downloaded data while still having access to the other resources of the PHR website when an Internet connection is available. In this regard, the patient's login name may be embedded into the index document and optionally accessible by clicking on a patient full name 80 as shown in FIG. 5. When the link 78 to the PHR website is invoked, this patient's login name 80 may be posted to the web site during the linking to provide an expedited connection to the patient's PHR records where the login name is pre-populated and the patient needs only to enter a password.

This ability to communicate with the PHR website using downloaded context further permits a link 78b to be created allowing the patient to easily check if the data represented by the medical data files 50 is current, or the degree to which the medical data files 50 are not current. By posting the date of the download, or a "fingerprint" of the file data, such as a hash, the PHR website may respond with a web page indicating whether the data is essentially current or not, or optionally whether important changes have been made to the data. This may be permitted, with some limitations, by any possessor of the medical data files 50, even those without permission to access the patient data 14 through the PHR website 10. Such a feature might be usable in an emergency situation, for example.

Referring again to FIGS. 3 and 4, once the augmented data files have been created per process block 63, the patient may be prompted to indicate whether the files should be password-protected at process block 90. Such password protection may not be normally implemented by the electronic medical file standards, but may be desired, for example, if the files are not being transferred immediately to another health care institution and are being used by the patient for an on-person medical record, for example if he or she is traveling or the like, as is made practical by the present invention. Password protection preserves the security of the documents, if, for example, the thumb drive holding the files is lost.

If password protection is desired, then a password is input by the patient at process block 91 and, as indicated by arrows 94 of FIG. 3, the files 50 are converted to password-protected files 96. Such password-protected files may, for example, be in the form of PDF files, readable by most browsers, but further limiting the ability of the files to be accidentally modified.

Referring now to FIGS. 2 and 4, at process block 100 the augmented and generated files, including the medical data files 50, the index file 54, an XML stylesheet 44, an index HTML stylesheet 102, and other mandated files 104 such as the README file 104, may be packaged and zipped to produce a downloadable file 110. This file may then be downloaded per conventional techniques as indicated by process block 112.

Figure 6:
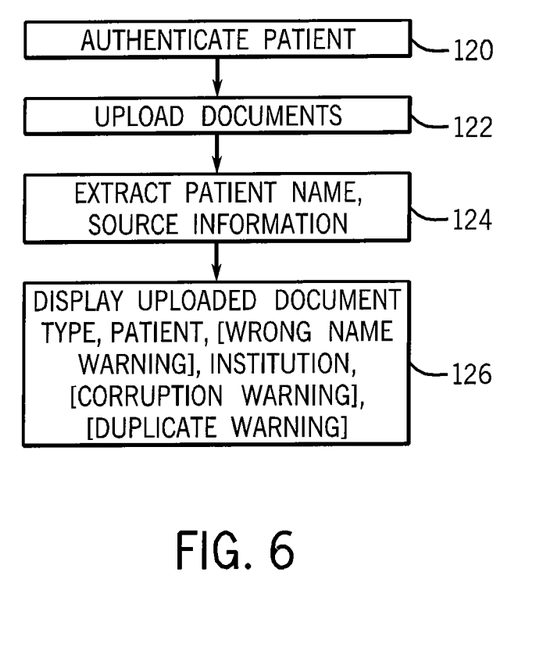
FIG. 6 is a flow chart showing enhancement of the uploading process by the PHR server computer of FIG. 1.

Referring now to FIG. 6, the above features of reading the medical data files to improve their accessibility suggests a similar technique for improving the uploading process for the patient when documents (such as CCD-compliant documents) are uploaded to the PHR website 10. As indicated by process block 120 and as executed by the computer 12 running PHR program 16, after authentication of the identity of a patient visiting the PHR website 10, a document to be uploaded may be identified as indicated by process block 122, for example, on a thumb drive or optical disk read by the computer 24 shown in FIG. 1.

The uploaded files may be placed in a temporary storage location on the computer 12 and, as indicated by process block 124, be interrogated to extract the patient name record 34 and the data source 40 fields from the files 50. At process block 126, each of the files together with extracted identifying information, including the patient name and the source institution name, may then be presented to the patient for confirmation that the correct files were uploaded. In this confirmation process the patient can view the name of the patient of the uploaded files to confirm that this is in fact the file he or she wishes to upload, this confirmation optionally being expressed as a warning if the patient identification used in the authentication of process block 120 differs from the patient name extracted from the files 50.

If the files are corrupted, as indicated by one or more error correction data blocks in the files, a corruption warning may be displayed. Further, the files may be reviewed to see if they are identical to previously uploaded files. Both of these situations can provoke a warning requiring an intentional patient override if uploading is to proceed.

It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

We claim:

1. A computer-implemented health-data-portal aggregator comprising:
   at least one electronic computer including memory coupled to a CPU, implementing a personal health record website connected to a computer network accessible by a patient using a standard browser, the electronic computer implementing a database for storage of medical records and executing a stored program to:
   (a) receive medical information from the patient for storage in the database;
   (b) receive clinical medical records of the patient from an electronic medical record system associated with at least one healthcare institution for storage in the database;
   (c) display to the patient over the computer network data from at least one of the medical information from the patient and the clinical records of the patient in one or more personal health record web pages including graphical elements and links to features of a personal health record website; and
   (d) generate a downloaded index file including patient medical data accessible by at least one HTML link, and selected from at least one of: (1) the medical information from the patient and (2) the clinical records of the patient, wherein the index file includes instructions to a browser interpreting HTML for displaying the patient medical data in a consistent presentation independent of whether the browser is connected to a network, wherein the downloaded index file is augmented with at least one of:
- (i) an HTML element displaying information generated based on the HTML link and derived from the content of the downloaded medical data the referenced by the HTML link;
- (ii) a graphical element of at least one of the personal health record web pages;
- (iii) a link to at least one element in the personal health record website;
- (iv) a stylesheet configured to modify a display of the patient medical data accessible by at least one HTML link to have the same look and feel as the personal health record web page, wherein the index file includes a link to the personal health record web page directing the aggregator to forward to the personal health record web page data associated with the downloaded medical data file necessary to establish whether a more current medical data file is present at the database for storage of medical records associated with the personal health record web page.

2. The health-data-portal aggregator of claim 1, wherein the index file includes a link to the personal health record web page, the link including information directing the aggregator to forward to the personal health record web page a patient identification for the personal health record web page used for authenticated access to the personal health record web page when combined with the password.

3. The health-data-portal aggregator of claim 1, wherein the downloaded patient medical data further includes a generic HTML stylesheet for a medical data file uploaded without an HTML stylesheet.

4. The health-data-portal aggregator of claim 1, wherein the electronic computer accepts input from the patient to reformat the downloaded medical data files for password protection.

5. The health-data-portal aggregator of claim 4, wherein reformatting the downloaded medical data files for password protection may be performed for less than all of the downloaded medical data files.

6. The health-data-portal aggregator of claim 1, wherein the electronic computer is further configured to execute the stored program to compare the downloaded index file and associated files to the files stored in the database for validation.

7. The health-data-portal aggregator of claim 6, wherein the comparison is performed based on an indication that the files are being uploaded to a second database for storage of medical records.

8. A health-data-portal aggregator comprising:
at least one electronic computer including memory coupled to a CPU, electronically implementing a personal health record website connected to a computer network accessible by a patient using a standard browser, the electronic computer implementing a database for storage of medical records and executing a stored program to:
- (a) accept medical information entered by the patient for storage on the electronic computer and display to the patient over the computer network as one or more personal health record web pages including graphical elements and links to features of the personal health record web page;
- (b) upload electronic clinical records generated by a healthcare institution in electronic format viewable in a browser interpreting HTML;
- (c) review the uploaded files to provide at least one caution to the patient with respect to the propriety of uploading the files based on the content of the files, wherein the caution is selected from the group consisting of: medical records for a patient with a different name than the patient of the personal health record website, corrupted medical records, duplicate medical records, and a display of the institution; and
- (d) generate a downloaded index file including patient medical data selected from at least one of: (1) the medical information from the patient and (2) the clinical records of the patient, wherein the index file includes instructions to a browser interpreting HTML for displaying the patient medical data in a consistent presentation independent of whether the browser is connected to a network, wherein the index file includes a link to the personal health record web page directing the aggregator to forward to the personal health record web page data associated with the downloaded medical data file necessary to establish whether a more current medical data file is present at the database for storage of medical records associated with the personal health record web page.

9. The health-data-portal aggregator of claim 8, wherein the index file includes a link to the personal health record web page, the link including information directing the aggregator to forward to the personal health record web page a patient identification for the personal health record web page used for authenticated access to the personal health record web page when combined with the password.

10. The health-data-portal aggregator of claim 8, wherein the downloaded patient medical data further includes a generic HTML stylesheet for a medical data file uploaded without an HTML stylesheet.

11. The health-data-portal aggregator of claim 8, wherein the electronic computer accepts input from the patient to reformat the downloaded medical data files for password protection.

12. The health-data-portal aggregator of claim 11, wherein reformatting the downloaded medical data files for password protection may be performed for less than all of the downloaded medical data files.

13. The health-data-portal aggregator of claim 8, wherein the electronic computer is further configured to execute the stored program to compare the downloaded index file and associated files to the files stored in the database for validation.

14. The health-data-portal aggregator of claim 13, wherein the comparison is performed based on an indication that the files are being uploaded to a second database for storage of medical records.

15. A computer-implemented method for generating a portable medical record, comprising:
- (a) receiving medical information from a patient for storage in a medical record database;
- (b) receiving clinical medical records of the patient from an electronic medical record system associated with at least one healthcare institution for storage in the medical record database;
- (c) displaying to the patient data, from at least one of the medical information from the patient and the clinical records of the patient, in one or more personal health record web pages including graphical elements and links to features of a personal health record website; and (d) generating a downloaded index file including patient medical data selected from at least one of: (1) the medical information from the patient and (2) the clinical records of the patient, wherein the index file includes instructions to a browser interpreting HTML for displaying the patient medical data in a consistent presentation independent of whether the browser is connected to a network, wherein the downloaded index file is augmented with at least one of:

(i) an HTML element displaying information generated based on the HTML link and derived from the content of the downloaded medical data file referenced by the HTML link;

(ii) a graphical element of at least one of the personal health record web pages;

(iii) a link to at least one element in the personal health record website;

(iv) a stylesheet configured to modify a display of the patient medical data accessible by at least one HTML link to be have the same look and feel as the personal health record web page, wherein the index file includes a link to the personal health record web page directing the aggregator to forward to the personal health record web page data associated with the downloaded medical data file necessary to establish whether a more current medical data file is present at the database for storage of medical records associated with the personal health record web page.

16. The computer-implemented method of claim 15, wherein the index file includes a link to the personal health record web page, the link including information directing the aggregator to forward to the personal health record web page a patient identification for the personal health record web page used for authenticated access to the personal health record web page when combined with the password.

17. The health-data-portal aggregator of claim 15, wherein the downloaded patient medical data further includes a generic HTML stylesheet for a medical data file uploaded without an HTML stylesheet.

18. The health-data-portal aggregator of claim 15, wherein the electronic computer accepts input from the patient to reformat the downloaded medical data files for password protection.

19. The health-data-portal aggregator of claim 18, wherein reformatting the downloaded medical data files for password protection may be performed for less than all of the downloaded medical data files.

20. The health-data-portal aggregator of claim 15, wherein the electronic computer is further configured to execute the stored program to compare the downloaded index file and associated files to the files stored in the database for validation.

21. The health-data-portal aggregator of claim 20, wherein the comparison is performed based on an indication that the files are being uploaded to a second database for storage of medical records.

* * * * *